(12) United States Patent
Mathieu et al.

(10) Patent No.: US 9,421,400 B2
(45) Date of Patent: Aug. 23, 2016

(54) METHOD FOR PREPARING A RECYCLABLE POLYAMIDE POWDER

(75) Inventors: Cyrille Mathieu, Rouen (FR); Gregory Filou, Manneville sur Risle (FR); Arnaud Lemaitre, Saint-Martin Saint-Firmin (FR)

(73) Assignee: ARKEMA FRANCE, Colombes (FR)

( * ) Notice: Subject to any disclaimer, the term of this patent is extended or adjusted under 35 U.S.C. 154(b) by 84 days.

(21) Appl. No.: 13/501,906

(22) PCT Filed: Oct. 18, 2010

(86) PCT No.: PCT/FR2010/052203
§ 371 (c)(1),
(2), (4) Date: Sep. 14, 2012

(87) PCT Pub. No.: WO2011/045550
PCT Pub. Date: Apr. 21, 2011

(65) Prior Publication Data
US 2013/0004448 A1    Jan. 3, 2013

(30) Foreign Application Priority Data

Oct. 16, 2009 (FR) ..................................... 09 57288

(51) Int. Cl.
| | | |
|---|---|---|
| *C08J 3/21* | (2006.01) | |
| *C08K 5/13* | (2006.01) | |
| *C08K 5/524* | (2006.01) | |
| *C08K 5/01* | (2006.01) | |
| *A61Q 1/10* | (2006.01) | |
| *A61K 8/88* | (2006.01) | |
| *C08J 3/12* | (2006.01) | |
| *C08J 3/205* | (2006.01) | |
| *C08K 5/00* | (2006.01) | |

(52) U.S. Cl.
CPC . *A61Q 1/10* (2013.01); *A61K 8/88* (2013.01); *C08J 3/12* (2013.01); *C08J 3/2053* (2013.01); *C08K 5/005* (2013.01); *C08K 5/01* (2013.01); *C08J 2377/00* (2013.01); *Y10T 428/2982* (2015.01)

(58) Field of Classification Search
CPC ............ A61K 8/88; A61Q 1/10; A61Q 1/00; C08J 3/12; C08J 3/2053; C08J 3/205
See application file for complete search history.

(56) References Cited

U.S. PATENT DOCUMENTS

| | | |
|---|---|---|
| 5,763,512 A | 6/1998 | Schmitter |
| 2003/0235666 A1* | 12/2003 | Buhler ........................ 428/35.7 |
| 2004/0106691 A1 | 6/2004 | Monsheimer et al. |
| 2006/0041041 A1 | 2/2006 | Douais et al. |
| 2006/0071359 A1 | 4/2006 | Monsheimer et al. |
| 2009/0075081 A1 | 3/2009 | Ouvrard et al. |

OTHER PUBLICATIONS

International Search Report of PCT/FR2010/052203 (Feb. 24, 2011).

* cited by examiner

*Primary Examiner* — Jessica Worsham
(74) *Attorney, Agent, or Firm* — Millen, White, Zelano and Branigan, P.C.

(57) ABSTRACT

A method for preparing a recyclable polyamide powder, including the following consecutive steps: a) a step of adding 0.01 to 5 wt % of at least one antioxidant in powder form to a mixture including 20 to 95 wt % of polyamide powder and 5 to 80 wt % of liquid, relative to the weight of said mixture, the polyamide powder having a pH in the range from 3 to 8 and a yellowness index of less than 4, measured according to standard ASTM E 313-05, D1925, the liquid being a non-solvent for polyamide at a temperature between 5° C. and the boiling temperature $T_{eb}$ of said liquid; b) a step of homogenizing the mixture obtained in step a); c) a step of recovering powder isolated from the liquid.

7 Claims, No Drawings

METHOD FOR PREPARING A RECYCLABLE POLYAMIDE POWDER

The present invention relates to a process for the manufacture of a polyamide-based powder, said powder having stable properties, that is to say not varying as a function of the temperature, and thus being able to be recycled.

The possibility of recycling the powder is desired in particular for processes for the manufacture of articles by agglomeration of powder by melting or sintering brought about by radiation, such as, for example, a laser beam (laser sintering), infrared radiation or UV radiation or any source of electromagnetic radiation. Such processes are described in the documents U.S. Pat. No. 6,136,948 and WO9606881. Recycled powder is understood to mean a powder which has already been used at least once in a process before being reused in this same process. Virgin powder is understood to mean a new powder which has never been used in a process for the manufacture of articles.

Polyamide-based powers is understood to mean pulverulent compositions comprising more than 50% by weight of polyamide (hereinafter abbreviated PA). Polyamide powders is understood to mean those comprising more than 95% by weight of polyamide. Polyamide powders can be produced by various processes which each result in different powder characteristics. Mention may be made of direct synthesis processes, which result, for example, in polyamide 12 powders by polymerization of lauryllactam or of aminododecanoic acid. Depending on the type of process, it is possible to obtain nonporous perfectly spherical powders or else porous spheroidal powders. In the latter case, mention may be made of the PA 12 powders sold by Arkema France under the Orgasol® name. There also exists dissolution/precipitation processes which result in polymer powders by dissolution of a polymer in a solvent, followed by reprecipitation in the powder form. Depending on their process of manufacture, the polyamide powders obtained are more or less white.

The lack of stability under certain conditions (for example temperature) of these polyamide powders, in particular their yellowing, presents a problem. The recycling of these powders then becomes restricted, and even impossible. The color of the parts manufactured with such a powder is not reproducible, since the color of the powder used varies over time. For the parts manufactured from these powders, the same problem of instability (of variation) in color may gradually appear over time.

Several methods have been provided for solving or at least masking this problem of instability of color of polyamide powders:

the addition of a whitening pigment ($TiO_2$) to a polyamide powder, either by compounding and then grinding in the powder form, or by compounding before dissolution/precipitation, or at the beginning of the dissolution/precipitation process (EP 1 411 087);

the addition of metal salts of monocarboxylic acids, such as sodium or calcium salts of saturated fatty acids, in particular of montanic acid (EP 1 424 354), or the addition of a metal salt of a weak acid and of a fatty acid, fatty ester or fatty amide derivative, such as EBS or ethylenebisstearylamide (EP 1 505 108). The addition takes place:

either by dry blending or by compounding in molten PA before grinding to form a powder;

or by mixing salts partially dissolved in a solvent and mixed with a solution of polyamide (dissolved or in suspension) before reprecipitation of the polyamide (if it is dissolved) or extraction of the solvent (if the PA is in suspension);

or by mixing salts with a solution of polyamide dissolved in ethanol before complete precipitation of the PA in the powder form;

the addition of antioxidant(s), such as phenolic and/or phosphate antioxidants, by compounding or dry blending;

washing the powder with ethanol, in order to remove the residual monomers, the oligomers and other impurities;

the addition of chain-limiting agents, of mono- or dicarboxylic acid type, during the polymerization in order to obtain limited PAs which are chemically stable during laser sintering processes and of stable molecular weight (WO05097475, EP 1 413 594).

In the abovementioned documents, the reduction in the yellowing is brought up only in the document EP 1 411 087, and it is not characterized but correlated solely with the stability of the DSC measurements of the powder or of the mechanical properties (for example of the modulus of elasticity) of the parts obtained from the powder. The stabilization methods described do not make it possible to obtain a powder having stable color capable of withstanding several significant variations in temperature. The result of this is that the powder cannot be recycled after one or more variations in temperature without variation in the yellowness index of the powder. "Several significant variations in temperature" should be understood as meaning at least three successive heating cycles, preferably at least five successive heating cycles, up to a temperature lower by 2° C. to 30° C. with respect to the melting point of the powder.

The aim of the present invention is thus to provide a process for the manufacture of a recyclable polyamide powder. Recyclable powder within the meaning of the invention is understood to mean a thermally stable powder, which thus does not turn yellow, that is to say for which the yellowness index YI does not vary by more than 2 units according to standard ASTM E 313-05, D1925, after several successive heating cycles (at least three cycles) at a temperature close to the melting point M.p. of said powder, that is to say at a temperature within the range extending from M.p. −30° C. to M.p. −2° C.

The Applicant Company has demonstrated that, surprisingly, the addition under certain conditions of an antioxidant to a polyamide in the pulverulent form, having a pH within the range extending from 3 to 8 and preferably having a yellowness index of less than 4, preferably of less than 3, makes it possible to manufacture a recyclable powder, resulting in articles identical in color, independently of the fact that the powder according to the invention is virgin or recycled.

A subject matter of the present invention is thus a process for the preparation of a recyclable polyamide-based powder, said process comprising the following successive stages:

a) a stage of addition of from 0.01 to 5% by weight, preferably from 0.01 to 1% by weight, of at least one antioxidant in the pulverulent form to a mixture comprising from 20 to 95% by weight of polyamide-based powder and from 5 to 80% by weight of liquid, with regard to the weight of said mixture, said polyamide powder of the mixture having a pH within the range extending from 3 to 8, preferably from 4 to 7, said polyamide-based powder of the mixture preferably having a yellowness index of less than 4, measured according to standard ASTM E 313-05, D1925, said liquid being a nonsolvent for the polyamide at a temperature of between 5° C. and the boiling point B.p. of said liquid;

b) a stage of homogenization of the mixture obtained in stage a);

c) a stage of recovery of powder isolated from the liquid.

Advantageously, the powder, that is to say both the initial powder of the mixture used in the process of the invention and the recyclable powder obtained by the process, has a mean diameter by volume within the range extending from 5 to 150 μm, preferably from 20 to 100 μm.

The powder used in the mixture of powder and liquid according to the process of the invention has a pH within the range extending from 3 to 8, preferably from 4 to 7. It is easy for a person skilled in the art to adjust the pH of the powder by adding a suitable amount of a buffer system or of an aqueous solution of an acid, for example hypophosphorous acid, of phosphoric acid, of citric acid or of salts of these acids. Methods for adjusting the pH of the powder commonly used are, for example, described in the documents EP 1 319 681, U.S. Pat. No. 6,281,282, US2003114636 and U.S. Pat. No. 839,165.

In the present description of the invention, the pH measurements are carried out according to standard ISO 787-9: 1981. Use is made, in particular in the examples below, of the Consort 833 pH meter and a low-conductivity electrode (Bioblock G90398 probe) for measuring the pH of the powder. In fact, the pH of a solution of ultrapure water after extraction of the salts present in the powder is measured. For this, 5 g of powder are mixed with 100 ml of ultrapure water of pH 7 with stirring (for 30 minutes) and then the pH of the solution is measured.

The powder used in the mixture of powder and liquid according to the process of the invention has a yellowness index of less than 4, preferably less than 3. Such powders with a yellowness index of less than 3 are sold by Arkema, in particular under the Orgasol®, Rilsan® and Pebax® brands and by Evonik, in particular under the Vestosint® brand.

Advantageously, said at least one antioxidant is chosen from phenolic antioxidants, phosphites and their mixtures.

Mention may be made, as an example of phenolic antioxidant, of 4,4'-butylidenebis(2-(t-butyl)-5-methylphenol), sold in particular under the name Lowinox 44B25 by Chemtura, pentaerythritol tetrakis(3-(3,5-di(tert-butyl)-4-hydroxyphenyl)propionate), sold in particular under the name Irganox® 1010 by Ciba, N,N'-hexane-1,6-diylbis(3-(3,5-di(tert-butyl)-4-hydroxyphenyl)propionamide), sold in particular under the name Irganox® 1098 by Ciba, 3,3',3",5,5',5"-hexa(tert-butyl)-α,α',α"-(mesitylene-2,4,6-triyl)tri (p-cresol), sold in particular under the name Irganox® 1330 by Ciba, ethylenebis(oxyethylene)bis(3-(5-(tert-butyl)-4-hydroxy-m-tolyl)propionate), sold in particular under the name Irganox® 245 by Ciba, 1,3,5-tris(3,5-di(tert-butyl)-4-hydroxybenzyl)-1,3,5-triazine-2,4,6(1H,3H,5H)trione, sold in particular under the name Irganox® 3114 by Ciba, N,N'-(2-ethyl-2'-ethoxyphenyl)oxanilide, sold in particular under the name Tinuvin® 312 by Ciba, phenol, 4,4',4"-[(2,4,6-trimethyl-1,3,5-benzenetriyl)tris(methylene)]tris[2,6-bis(1,1-dimethylethyl)]-, sold in particular under the name Alvinox® 1330 by 3V, Hostanox 245 FF, Hostanox 245 Pwd, sold by Clariant, pentaerythritol tetrakis(3-(3,5-di(tert-butyl)-4-hydroxyphenyl)propionate), sold in particular under the names Evernox 10 and Evernox 10GF by Everspring Chemical Company Limited, octadecyl 3-(3,5-di(tert-butyl)-4-hydroxyphenyl)propionate, sold in particular under the names Evernox 76 and Evernox 76GF by Everspring Chemical Company Limited, tetrakis-[methylene-3-(3',5'-di(tert-butyl)-4-hydroxyphenyl)-propionate]methane, sold in particular under the name BNX® 1010 by Mayzo, thiodiethylene bis[3-(3,5-di(tert-butyl)-4-hydroxyphenyl)propionate], sold in particular under the name BNX® 1035 by Mayzo, tetrakis[methylene-3-(3',5'-di(tert-butyl)-4-hydroxyphenyl)propionate]-methane, octadecyl 3-(3,5-di(tert-butyl)-4-hydroxy-phenyl)propionate, sold in particular under the name BNX® 2086 by Mayzo, or 1,3,5-tris(3,5-di(tert-butyl)-4-hydroxybenzyl)-1,3,5-triazine-2,4,6(1H,3H,5H)-trione, sold in particular under the name BNX® 3114 by Mayzo.

Mention may be made, as an example of phosphite (phosphite antioxidant), of tris(2,4-di(tert-butyl)phenyl) phosphite, sold in particular under the names Irgafos® 168 by Ciba, CSFC 186 by China Scientific Fine Chemicals, Everfos 168 by Everspring Chemical Company Limited and Benefos® 1680 by Mayzo.

Mention may be made, as an example of antioxidant which is simultaneously a phenolic and phosphite antioxidant, of the mixture of tetrakismethylene(3,5-di(tert-butyl)-4-hydroxyhydrocinnamate)methane and tris(2,4-di(tert-butyl)phenyl)phosphite, sold in particular under the names Anox BB 2777, Anox BB 2888, Anox BB 011 and Anox BB 021 by Chemtura (Great Lakes), or the mixture of 20% stearyl 3-(3,5-di(tert-butyl)-4-hydroxyphenyl)-propionate and 80% tris(2,4-di(tert-butyl)phenyl)phosphite, sold in particular under the name BNX® 1900 by Mayzo.

The antioxidants preferred for the present invention are the phenolic antioxidants as they exhibit the advantage of being stable and of not decomposing under a temperature close to the melting point of the polyamide-based powders. Consequently, they do not leave residues when they are subjected to temperatures close to the melting point of the polyamide-based powders, in particular when they are used in a laser sintering machine. On the contrary, it happens that phosphite antioxidants leave residues which foul the sintering machine in the parts of the machine which are not in contact with the powder, in particular the optical parts of the machine.

Preferably, the addition stage a) is carried out at a temperature within the range extending from 15 to 105° C., preferably from 50 to 90° C.

Preferably, the homogenization stage b) comprises the following successive stages:

b1) a phase of heating said mixture obtained in stage a) up to a temperature within the range extending from 50 to 120° C., preferably from 60 to 90° C.;

b2) a hot isothermal stage with stirring, during which the temperature of the mixture is kept constant, within the range of temperatures extending from 50 to 120° C., preferably from 60 to 90° C., for a time sufficient to homogenize the entire mixture.

The stage c) of recovery of the powder can comprise any solid/liquid separation (powder/liquid separation) means, for example by filtration, and/or any means for drying the power, in particular by evaporation of the liquid.

Advantageously, the stage c) of recovery of powder comprises the following successive stages:

c1) a phase of heating said homogeneous mixture obtained in stage b) up to a temperature between the boiling point of said liquid and the melting point of the powder;

c2) a hot isothermal phase during which the temperature of the mixture is kept constant, between the boiling point of said liquid and the melting point of the power, for a time sufficient to make it possible for all of the liquid to evaporate and to obtain a recyclable powder according to the invention.

In stage c), alternatively, additionally or simultaneously, the powder is dried under reduction in pressure, so as to reduce the boiling point of the liquid and so that stage c) is carried out at a lower temperature, that is to say at a temperature of the order of 80 to 100° C., for example at 90° C.

Advantageously, said liquid of the mixture has (at atmospheric pressure) a boiling point B.p. within the range extending from 70 to 170° C., preferably from 85 to 170° C., preferably from 120 to 170° C. Preferably said liquid comprises a hydrocarbon fraction, such as isoparaffins, preferably comprising from 6 to 12 carbon atoms per molecule and with a boiling point of at least 120° C. Mention may in particular be made of the mixtures of isoparaffin, of n-paraffin and of cycloparaffin having a boiling range lying between 140 and 170° C.

Another subject matter of the present invention is a polyamide-based powder having a melting point M.p. capable of being manufactured according to the process of the invention, said powder having a pH within the range extending from 3 to 8, preferably from 4 to 7, and a stable yellowness index YI (measured according to standard ASTM E 313-05, D1925) not varying by more than 3 units, preferably not varying by more than 2 units, after at least three successive heating cycles, preferably after at least five successive heating cycles, at a temperature within the range extending from M.p. −30° C. to M.p. −2° C., said powder comprising from 0.01 to 5% by weight and preferably from 0.01 to 1% by weight of at least one antioxidant. In the present description, the melting point M.p. of the powder corresponds to the melting point in first heating of the powder, measured according to standard ISO 11357-3 Plastics-Differential scanning calorimetry (DSC), Part 3. Preferably, said powder according to the invention has a yellowness index of less than 4, preferably of less than 3.

Advantageously, said polyamide-based powder according to the invention comprises at least one homopolyamide and/or at least one copolyamide and/or at least one copolyesteramide and/or at least one copolymer having polyamide blocks and polyether blocks (abbreviation PEBA) and/or their blends.

Advantageously, said polyamide-based powder comprises at least one monomer chosen from aminocarboxylic acids, preferably $\alpha,\omega$-aminocarboxylic acids, comprising from 4 to 18 carbon atoms, diamine.diacid pairs comprising from 4 to 18 carbon atoms, lactams comprising from 3 to carbon atoms, lactones comprising from 3 to 18 carbon atoms and their mixtures.

According to a preferred embodiment of the invention, said polyamide-based particles comprise at least one polyamide and/or at least one copolyamide and/or at least one copolyesteramide and/or their blends.

Polyamide (homopolyamide or copolyamide) within the meaning of the invention is understood to mean the condensation products of lactams, of amino acids and/or of diacids with diamines and generally any polymer formed by units or monomers connected to one another via amide groups.

Copolyesteramides are understood to mean the polymers resulting from the copolymerization of lactam(s) with one or more lactone(s), as described in patent EP 1 172 396.

The term "monomer" in the present description of the polyamide-based powders should be taken within the meaning of "repeat unit". The case where a repeat unit of the polyamide is composed of the combination of a diacid with a diamine is specific. It is considered that it is the combination of a diamine and of a diacid, that is to say the diamine.diacid pair (in an equimolar amount), which corresponds to the monomer. This is explained by the fact that, individually, the diacid or the diamine is only a structural unit, which is not sufficient in itself alone to polymerize. In the case where the particles of powder according to the invention comprise at least two different monomers, known as "comonomers", that is to say at least one monomer and at least one comonomer (monomer different from the first monomer), they comprise a copolymer, such as a copolyamide, abbreviation CoPA, or else a copolyesteramide, abbreviation CoPEA.

Mention may be made, as an example of lactams, of those having from 3 to 12 carbon atoms on the main ring and which can be substituted. Mention may be made, for example, of $\beta,\beta$-dimethylpropiolactam, $\alpha,\alpha$-dimethylpropiolactam, amylolactam, caprolactam, capryllactam, oenantholactam, 2-pyrrolidone and lauryllactam.

Mention may be made, as an example of diacid (or dicarboxylic acid), of the acids having between 4 and 18 carbon atoms. Mention may be made, for example, of adipic acid, sebacic acid, azelaic acid, suberic acid, isophthalic acid, butanedioic acid, 1,4-cyclohexanedicarboxylic acid, terephthalic acid, the sodium or lithium salt of sulphoisophthalic acid, dimerized fatty acids (these dimerized fatty acids have a dimer content of at least 98% and are preferably hydrogenated) and dodecanedioic acid HOOC—$(CH_2)_{10}$—COOH.

Mention may be made, as an example of diamine, of aliphatic diamines having from 6 to 12 atoms; they can be arylic and/or saturated cyclic. Mention may be made, as examples, of hexamethylenediamine, piperazine, tetramethylenediamine, octamethylenediamine, deca-methylenediamine, dodecamethylenediamine, 1,5-diaminohexane, 2,2,4-trimethyl-1,6-diaminohexane, polyol-diamines, isophoronediamine (IPD), methylpenta-methylenediamine (MPDM), bis(aminocyclohexyl)methane (BACM), bis(3-methyl-4-aminocyclohexyl)methane (BMACM), meta-xylenediamine, bis(p-aminocyclohexyl)methane and trimethylhexamethylenediamine.

Mention may be made, as an example of amino acid, of $\alpha,\omega$-amino acids, such as aminocaproic acid, 7-aminoheptanoic acid, 11-aminoundecanoic acid, n-heptyl-11-aminoundecanoic acid and 12-aminododecanoic acid.

Mention may be made, as an example of lactone, of caprolactone, valerolactone and butyrolactone.

The monomer(s) preferably used in the invention is or are chosen from lactams, such as, for example, lauryllactam, caprolactam, oenantholactam, capryllactam or their mixtures. Preferably, use is made of lauryllactam, alone or as a mixture with caprolactam.

The polymerization between the various abovementioned monomers can be of the hydrolytic polycondensation, anionic polymerization or also cationic polymerization type. The hydrolytic polymerization, in particular used for lactams, is induced by high-temperature water. For example, the hydrolytic polymerization of lactams consists in opening the lactam with water and then heating under pressure in order to polymerize. Optionally, a catalyst, such as phosphoric acid, can also be employed in the hydrolytic process. The anionic polymerization is carried out at temperatures far below those applied for the hydrolytic or cationic mechanisms. Anionic polymerization is carried out continuously or else, preferably, batchwise in a solvent. The anionic route relates more specifically to cyclic molecules, such as lactams and lactones. For example, the mechanism for the anionic polymerization of lactams takes place in three stages: an initiation stage, to form the lactamate anion, then an activation reaction, which results in the acyllactam, and, finally, the propagation stage. The anionic polymerization method is thus based essentially on the use of a catalyst and of an activator in the presence optionally of a finely divided inorganic or organic filler having a role of crystallization seed and in the presence of an amide. The process is described in patents EP 192 515 and EP 303 530. The cationic polymerization is catalyzed by acids under anhydrous conditions. In this case, acids, such as hydrochloric acid, phosphoric acid or hydrobromic acid, are the most reactive but the use of Lewis acids or of ammonium salts is also possible. There essentially exist two types of activation and of growth of the chain. Either the activated monomer reacts with the neutral reactive center or it is the reactive center which is activated and the monomer neutral.

Preferably, the recyclable polyamide-based powders of the invention comprise at least one polyamide chosen from polyamides and copolyamides comprising at least one of the following monomers: 4.6, 4.T, 5.4, 5.9, 5.10, 5.12, 5.13, 5.14, 5.16, 5.18, 5.36, 6, 6.4, 6.9, 6.10, 6.12, 6.13, 6.14, 6.16, 6.18, 6.36, 6.T, 9, 10.4, 10.9, 10.10, 10.12, 10.13, 10.14, 10.16, 10.18, 10.36, 10.T, 11, 12, 12.4, 12.9, 12.10, 12.12, 12.13, 12.14, 12.16, 12.18, 12.36, 12.T, and their mixtures; in particular chosen from PA 11, PA 12, PA 10.10, PA 6, PA 6/12, PA 11/10.10 and their mixtures.

According to another advantageous embodiment of the invention, said polyamide-based particles comprise at least one copolymer comprising polyamide blocks and polyether blocks or polyether-block-amide, abbreviation PEBA. PEBAs result from the polycondensation of polyamide blocks comprising reactive ends with polyether blocks comprising reactive ends, such as, inter alia:
1) polyamide blocks comprising diamine chain ends with polyoxyalkylene blocks comprising dicarboxyl chain ends,
2) polyamide blocks comprising dicarboxyl chain ends with polyoxyalkylene blocks comprising diamine chain ends obtained by cyanoethylation and hydrogenation of aliphatic α,ω-dihydroxylated polyoxyalkylene blocks, known as polyetherdiols,
3) polyamide blocks comprising dicarboxyl chain ends with polyetherdiols, the products obtained being, in this particular case, polyetheresteramides.

The polyamide blocks comprising dicarboxyl chain ends originate, for example, from the condensation of polyamide precursors in the presence of a chain-limiting dicarboxylic acid. The polyamide blocks comprising diamine chain ends originate, for example, from the condensation of polyamide precursors in the presence of a chain-limiting diamine. The number-average molar mass Mn of the polyamide blocks is within the range extending from 400 to 20 000 g/mol, preferably from 500 to 10 000 g/mol and more preferably from 600 to 6000 g/mol.

The polymers comprising polyamide blocks and polyether blocks can also comprise randomly distributed units.

The polyamide blocks can comprise homopolyamides or copolyamides, such as those described above in the present description.

Polyether (hereinafter abbreviated PE) blocks within the meaning of the invention are understood to mean polyalkylene ether polyols, in particular polyalkylene ether diols. The polyether (PE) blocks comprise at least one polymer chosen from poly(ethylene glycol) (PEG), poly(1,2-propylene glycol) (PPG), poly(1,3-propylene glycol) (PO3G), poly(tetramethylene glycol) (PTMG), poly(hexamethylene glycol), poly(1,3-propylene glycol) (PO3G), poly(3-alkyltetrahydrofuran)s, in particular poly(3-methyltetrahydrofuran)(poly (3MeTHF)), and their copolymers or blends. It is also possible to envisage a PE block of block or random "copolyether" type comprising a sequence of at least two abovementioned types of PE.

The polyether blocks can also comprise blocks obtained by oxyethylation of bisphenols, such as, for example bisphenol A. The latter products are described in patent EP 613 919.

The polyether blocks can also comprise ethoxylated primary amines. Use is also advantageously made of these blocks. Mention may be made, as an example of ethoxylated primary amines, of the products of formula:

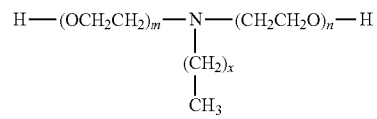

in which m and n are between 1 and 20 and x is between and 18. These products are available commercially under the Noramox® brand from Ceca and under the Genamin® brand from Clariant.

Thus, the chain ends of the PE blocks can be diOH, $diNH_2$, diisocyanate or diacid, according to their process of synthesis.

The PE blocks comprising $NH_2$ chain ends can be obtained by cyanoacetylation of aliphatic α,ω-dihydroxylated polyoxyalkylene sequences, known as polyetherdiols, such as Jeffamines® D300, D400, D2000, ED-600, ED-900 or ED2003 or Elastamines® RP-409, RP-2009, RT-1000, RE-600, RE-900, RE-2000, HT-1700 or HE-180 from Huntsman. Such blocks are described in patents JP 2004346274, JP 2004352794 and EP 1 482 011. The molar mass Mn of the polyether blocks is within the range extending from 100 to 6000 g/mol, preferably from 200 to 3000 g/mol and more preferably still from 250 to 2000 g/mol.

The preparation of the copolymers comprising polyamide block(s) and polyether block(s) according to the invention comprises any means which makes it possible to attach polyamide blocks (PA block) and polyether blocks (PE block). In practice, use is essentially made of two processes, one a "two-stage" process and the other a "one-stage" process; these two processes are well known and are described, for example, in patent application FR0856752.

Advantageously, the polyamide-based powders of the invention comprise at least one copolymer comprising polyamide blocks and polyether blocks chosen from: PA12-PEG, PA6-PEG, PA6/12-PEG, PA11-PEG, PA12-PTMG, PA6-PTMG, PA6/12-PTMG, PA10.10-PEG, PA10.10-PTMG, PA11-PTMG, PA12-PEG/PPG, PA6-PEG/PPG, PA6/12-PEG/PPG, PA11-PEG/PPG and their blends.

Depending on the method of synthesis for the polymers described above, powder or else granules is/are obtained directly. Powder is obtained directly by anionic polymerization. In order to obtain polyamide-based powder in the case of the other types of polymerization, mention may be made, for example, of dissolution/precipitation, that is to say dissolution of the polyamide-based polymer in a solvent under hot conditions, followed by precipitation of the powder by slow cooling. Such a process is described, for example, in the document DE2906647. Mention may also be made of atomization, that is to say the spraying of a solution of the cooled polymer. This technique is also known as "cold nebulization" or "spray cooling". There also exists a process for extrusion of polymer, followed by atomization by a heated high-pressure nozzle, then cooling of the powder obtained. This technique is also known as "hot nebulization" or "spray drying". Mention may also be made of the grinding/sieving of polymer granules, optionally followed by a rise in viscosity. The grinding can be cryogenic. All these techniques for producing powder are already well known to a person skilled in the art.

Advantageously, said particles of polyamide-based powder of the invention have a median diameter by volume within the range extending from 5 to 150 µm, preferably from 20 to 100 µm.

Advantageously, said powder results at least partially from renewable or bioresourced materials; it then comprises $^{14}C$, this content of biocarbon being determined in accordance with the standard ASTM D 6866.

Advantageously, the powder according to the invention additionally comprises at least one additive chosen from: optical brighteners, pigments, dyes, stabilizers, including UV stabilizers, flame retardants, flow agents, organic or inorganic fillers, silica powder, powder binders, carbon nanotubes and their mixtures.

Another subject matter of the present invention is a process for the manufacture of articles by agglomeration of polyamide-based powder, by melting using electromagnetic radiation, the polyamide-based powder having been obtained beforehand according to the process defined above.

A fine layer of polyamide powder is deposited on a horizontal plate maintained in a chamber heated at a temperature lying between the crystallization point C.p. and the melting point M.p. of the polyamide powder. The laser agglomerates powder particles at different points in the powder layer according to a geometry corresponding to the article, for example using a computer which has the shape of the article in memory and which recreates this shape in the form of slices. The horizontal plate is subsequently lowered by a value corresponding to the thickness of a powder layer (for example, between 0.05 and 2 mm and generally of the order of 0.1 mm), then a fresh powder layer is deposited and the laser agglomerates powder particles according to a geometry corresponding to this new slice of the object, and so on. The procedure is repeated until the complete article has been manufactured. An article surrounded by powder is obtained inside the chamber. The parts which were not agglomerated have thus remained in the powder form. Subsequently, the combined product is gently cooled and the article solidifies as soon as its temperature falls below the crystallization point C.p. When completely cooled, the article is separated from the powder, which can be reused, optionally mixed with an additional amount of virgin powder, in another operation. Advantageously, the powder according to the invention can be recycled and reused as such, without the addition of virgin powder. In the process of the manufacture of articles by agglomeration of powder by melting according to the invention, the addition of a percentage of additional virgin powder within the range from 0 to 30% is amply sufficient to produce articles with colors and mechanical properties which are stable and reproducible.

Another subject matter of the present invention is thus a manufactured article having a stable color, said article being obtained by melting a powder in accordance with the invention using electromagnetic radiation.

Although, according to a preferred embodiment, the powder according to the invention is particularly well suited to use in processes for the manufacture of articles by melting or sintering brought about by electromagnetic radiation, the use of the powder of the invention can, of course, be envisaged in any other field which requires a powder having the same advantageous properties of color stability.

Another subject matter of the present invention is thus the use of the powder as defined above in cosmetic, pharmaceutical or perfumery products. A particular subject matter of the present invention is a cosmetic powder as defined above, characterized in that it constitutes a blusher or eyeshadow.

Another subject matter of the present invention is the use of the powder according to the invention in coatings, composites, structural adhesives, paints, corrosion-inhibiting compositions, paper additives, technologies for the agglomeration of powder by melting or sintering brought about by radiation in order to manufacture articles, electrophoresis gels, multilayer composite materials, the packing industry, furniture, domestic electrical appliances, toys, the textile industry, the automobile industry and/or the electronics industry.

EXAMPLES

The examples below illustrate the present invention without limiting the scope thereof. In the tests (examples and comparative examples below), unless otherwise indicated, all the percentages and parts are expressed by weight.

The powder used in the tests below is based on polyamide 12 (PA 12) manufactured according to the process described in the document EP 1 814 931. Its median diameter by volume is 45.8 µm.

The antioxidant used in the examples or comparative examples is a phenolic antioxidant, Lowinox 44B25 (4,4'-butylidenebis(2-(t-butyl)-5-methylphenol)), sold by Chemtura. The antioxidant is sometimes abbreviated to "AO" in the tables below.

The liquid used is a solvent, Shellsol D25, also sold under the name Gasoline 140/165, a hydrotreated light naphtha petroleum fraction, having CAS No. 64742-49-0.

In all the tests below, the yellowness index (abbreviation YI) is measured according to standard ASTM E 313-05, D1925, using the reference illuminant D65. A Konica-Minolta CM-3600d spectrometer is used. The uncertainty with regard to this measurement is less than 0.4. This means that, if the difference between two YI values is greater than 0.4, then the two values will be significantly different.

The yellowness index is measured for powders which have been subjected to from 0 to 3 (or up to 5) heating cycles at a temperature of between M.p. −30 and M.p. −2° C. These results are given in tables 1 and 3.

The yellowness index is measured for parts (in this instance, test specimens) manufactured by laser sintering from powders which have already been subjected to from 0 to 3 (or up to 5) heating cycles at a temperature of between M.p. −30 and M.p. −2° C. These results are given in tables 2 and 4.

In the following example 1 and comparative examples 1, 2 and 3, the same amount of antioxidant is added: i.e. 0.5% by weight of antioxidant with respect to the dry powder.

Example 1

The pH of the PA 12 powder is adjusted to 7 using a hypophosphorous acid solution. The yellowness index of the PA 12 powder used is less than 4. The antioxidant is added to a mixture comprising 90% by weight of PA 12 powder and 10% by weight of Shellsol D25.

Comparative Example 1

The pH of the PA 12 powder is adjusted to 7 in the same way as in example 1 but the yellowness index of the powder used is greater than 4. 0.5% of antioxidant is mixed with this PA 12 powder according to a conventional dry blending process.

Comparative Example 2

The pH of the PA 12 powder is adjusted to 7 in the same way as in example 1. The yellowness index of the PA 12 powder used is less than 4. 0.5% of antioxidant is mixed with this PA 12 powder according to a conventional dry blending process.

Comparative Example 3

The pH of the PA 12 powder is not adjusted to 7; it is greater than 8. The yellowness index of the PA 12 powder used is less than 4. The antioxidant is added to a mixture comprising 90% by weight of this PA 12 powder and 10% by weight of Shellsol D25.

The yellowness index is measured for these powders which have been subjected to from 0 to 3 heating cycles at a temperature of between M.p. −30 and M.p. −2° C. These results are given in table 1.

TABLE 1

| Test | pH of the powder | Anti-oxidant (%)/ addition process | Yellowness index YI (standard E313-05) of the powder: | | | | |
|---|---|---|---|---|---|---|---|
| | | | used in the antioxidant addition process | before heating phase | after 1 heating phase | after 2 heating phases | after 3 heating phases |
| Ex. 1 | 3-8 | 0.5/Inv | <4 | 1.2 | 2.2 | 2.8 | 2.8 |
| Comp. 1 | 3-8 | 0.5/DB | >4 | 4.3 | 6.8 | 6.9 | 7 |
| Comp. 2 | 3-8 | 0.5/DB | <4 | 2.2 | 3.7 | 4.2 | 4.6 |
| Comp. 3 | >8 | 0.5/Inv | <4 | 3.5 | 13.1 | | |

Example 1 according to the process of the invention makes it possible to obtain a recyclable powder having a low yellowness index (less than 3), the yellowness index of which does not increase by more than 2 units, even after several recyclings, in this instance at least three heating cycles.

Comparative examples 1 to 3 do not meet all the conditions of the antioxidant addition process according to the invention, using:
  either a starting polyamide with a yellowness index of greater than 4 (Comp. 1),
  or a process for mixing by dry blending (DB) (Comp. 2),
  or a process for addition of the antioxidant according to the invention (Inv), except for the fact that the polyamide of the mixture has a pH not included within the range 3-8 (Comp. 3).

These comparative examples 1 to 3 give a final powder which is either too yellow (YI>4), even before a first heating cycle (Comp. 3), or which turns yellow very quickly from the first heating cycles (Comp. 1 and 2: variation in YI of greater than 2 after three heating cycles).

At the same time, 3D articles, in this instance test specimens, with dimensions in accordance with the standard ISO 527 1B, are manufactured by laser sintering (sometimes abbreviated to "LS" in the tables) from the powder of example 1 which has been respectively subjected to 1, 2 and 3 heating phases in a laser sintering machine having the Formiga P100 EOS brand, that is to say, respectively:
  from virgin powder which is subjected to a heating phase above the melting point M.p. of the powder in the machine for manufacturing the test specimen,
  from recycled powder which has already been subjected to one heating phase at a temperature from M.p. −30° C. to M.p. −2° C. and which is subjected to a final heating phase at a temperature greater than the melting point M.p. of the powder in order to manufacture the test specimen,
  from recycled powder which has already been subjected to two heating phases at a temperature from M.p. −30° C. to M.p. −2° C. and which is subjected to a final heating phase at a temperature greater than the melting point M.p. of the powder in order to manufacture the test specimen.

It was not necessary, in order to carry out these tests, to add virgin powder to the recycled powder in the LS machine after each sintering cycle as sufficient recycled powder remained for the manufacture of the following part (the following sintering cycle). By virtue of the recyclable powder according to the invention, a percentage of additional virgin powder within the range from 0 to 30% is sufficient. In the tests described here, it is 0%.

TABLE 2

| | Yellowness index YI (standard E313-65) for the part manufactured from the powder which has been subjected to: | | |
|---|---|---|---|
| | 1 heating phase virgin powder | 2 heating phases recycled powder | 3 heating phases recycled powder |
| Part manufactured from the powder of example 1 | 1.4 | 2.6 | 2.9 |

The test specimens obtained with the powder of example 1 have a stable color, their yellowness index remaining below 3 and not varying by more than 2 units between each test specimen successively manufactured with increasingly recycled powder of example 1 (up to three heating phases).

The yellowness index of powders of the following example 2 (according to the invention) is subsequently compared with that of the powders of the comparative examples 2 and 4 (table 3); then the yellowness index of parts obtained from these powders (table 4 below):

Example 2

The pH of the PA 12 powder manufactured according to the process described in the document EP 1 814 931 is adjusted to 7 using a hypophosphorous acid solution. The yellowness index of the PA 12 powder is less than 4. The polyamide 12 powder is charged to a drier in which the antioxidant (Lowinox 44B25) has already been placed according to an amount by weight corresponding to 0.5% with respect to the dry powder or 0.4% with respect to the mixture of powder and liquid (Shellsol D25) according to the process of the invention. The charge of the drier is 48 kg of filtered powder with a residual solids content of 89.5%, which corresponds to a mixture according to the process of the invention (a mixture comprising from 20 to 95% by weight of polyamide-based powder and from 5 to 80% by weight of liquid). The weight of antioxidant Lowinox 44B25 charged beforehand to the drier is 215 g.

The temperature of the mixture is raised to 80° C. with stirring then maintained at 80° C. for 1 hour. After this stationary phase, without halting either the stirring or the heating, the final drying is carried out:

the temperature of the mixture is raised to 95° C. and, at the same time, the drier is placed under vacuum at 50 mbar, the drying is continued, the distillates collected in a keg positioned on a balance being weighed, the drying is halted when the weight of the keg has stabilized for 1 h.

The drier is brought back to atmospheric pressure and ambient temperature, and then emptied. A stabilized recyclable polyamide 12 powder is obtained according to the process of the invention.

Comparative Example 4

The pH of the PA 12 powder is adjusted to 7 in the same way as in example 2. The yellowness index of the PA 12 powder used is less than 4. However, in this test, antioxidant is not added.

Comparative Example 2

The pH of the PA 12 powder is adjusted to 7 in the same way as in example 2. The yellowness index of the PA 12 powder used is less than 4; it is 1.7.

1.5 kg of antioxidant Lowinox 44B25 are added to 300 kg of this PA 12 powder in a flobin.

The mixture obtained is homogenized at ambient temperature for 4 hours by rotating the flobin over itself (dry blending).

Comment: the mixture obtained in comparative example 2 exhibits a satisfactory homogenization: the product, subjected to an oven temperature of 174° C. under oxygen, does not exhibit colored oxidation points, in contrast to nonadditivated powder (comparative example 4).

TABLE 3

| Test | AO (44B25) % | Addition method | Virgin powder before use in LS run 0 | After 1 heating phase | After 2 heating phases | After 3 heating phases run 3 | After 5 heating phases | Change in the YI between run 0 and run 3 | |
|---|---|---|---|---|---|---|---|---|---|
| Comparative example 4 | 0 | — | 1.7 | 3.3 | 4.7 | 6.4 | — | 4.7 | Without AO addition |
| Comparative example 2 | 0.5 | DB | 2.2 | 3.7 | 4.2 | 4.6 | — | 2.4 | AO addition in dry blending |
| Example 2 | 0.5 | Inv | 1.1 | 2.2 | 2.3 | 2.1 | 2.4 | 1 | AO addition according to the invention |

Powder YI (standard E313-05, D65)

As seen in table 3, in contrast to comparative examples 2 and 4, example 2 according to the process of the invention makes it possible to obtain a recyclable powder having a low yellowness index (less than 3), the yellowness index of which does not increase by more than 2 units even after several recyclings, in this instance after at least five heating cycles in table 3.

TABLE 4

Parts YI (standard E313-05, D65)

| Test | AO (44B25) % | Addition method | After 1 heating phase run 1 | After 2 heating phases | After 3 heating phases | After 5 heating phases run 5 | Change in the YI between run 1 and run 5 | |
|---|---|---|---|---|---|---|---|---|
| Comparative example 4 | — | — | 3.1 | 2.9 | 4.7 | 7.3 | 4.2 | Without AO addition |

TABLE 4-continued

| Test | AO (44B25) % | Addition method | Parts YI (standard E313-05, D65) | | | | | |
|---|---|---|---|---|---|---|---|---|
| | | | After 1 heating phase run 1 | After 2 heating phases | After 3 heating phases | After 5 heating phases run 5 | Change in the YI between run 1 and run 5 | |
| Comparative example 2 | 0.5 | DB | 3.8 | 4.6 | 5.2 | 6.1 | 2.3 | AO addition in dry blending |
| Example 2 | 0.5 | Inv | 0.7 | 0.8 | 1.1 | 1.6 | 0.9 | AO addition according to the invention |

As seen in table 4, in contrast to the test specimens obtained with the powder of comparative examples 2 and 4, the test specimens obtained with the powder of example 2 have a stable color and their yellowness index remains in this instance less than 3 and does not vary by more than 2 units between each test specimen successively manufactured with increasingly recycled powder of example 2, in this instance after at least five heating cycles in table 4.

The invention claimed is:

1. A process for the preparation of a recyclable polyamide-based powder, said process comprising, successively,
   a) adding, at a temperature of 15 to 105° C., 0.01 to 5% by weight of at least one antioxidant in pulverulent form to a mixture comprising from 20 to 95% by weight of polyamide-based powder having a mean diameter by volume of 5 to 150 µm and from 5 to 80% by weight of liquid, with regard to the weight of said mixture, said polyamide-based powder of the mixture having a pH of 3 to 8 and a yellowness index of less than 4, measured according to standard ASTM E 313-05, D1925, said liquid comprising a hydrocarbon fraction, wherein the hydrocarbon fraction is an isoparaffin or a mixture of isoparaffins, n-paraffins or cycloparaffins, and being a nonsolvent for the polyamide at a temperature of between 5° C. and the boiling point B.p. of said liquid;
   b) homogenizing of the mixture obtained in a); and
   c) recovering recyclable powder isolated from the liquid.

2. The process as claimed in claim 1, in which said at least one antioxidant is a phenolic antioxidant, a phosphite or a mixture thereof.

3. The process as claimed in claim 1, in which homogenization b) comprises, successively,
   b1) heating said mixture obtained in a) up to a temperature of 50 to 120° C., and
   b2) hot isothermal stirring, during which the temperature of the mixture from b1 is kept constant, at temperatures of 50 to 120° C., for a time sufficient to homogenize the entire mixture.

4. The process as claimed in claim 1, in which c) of recovery of powder comprises, successively,
   c1) heating said homogeneous mixture obtained in stage b) up to a temperature between the boiling point of said liquid comprising a hydrocarbon fraction and the melting point of the powder; and
   c2) hot isothermal evaporation during which the temperature of the mixture is kept constant, between the boiling point of said liquid comprising a hydrocarbon fraction and the melting point of the powder, for a time sufficient to make it possible for all of the liquid to evaporate and to obtain a powder.

5. The process as claimed in claim 1, in which said polyamide-based powder comprises at least one monomer that is an aminocarboxylic acid comprising from 4 to 18 carbon atoms, a diamine.diacid pair comprising from 4 to 18 carbon atoms, a lactam comprising from 3 to 18 carbon atoms, a lactone comprising from 3 to 18 carbon atoms or mixtures thereof.

6. The process as claimed in claim 1, wherein the isoparaffin has 6-12 C atoms and a boiling point of at least 120° C.

7. The process according to claim 1, wherein the mixture of isoparaffins, n-paraffins or cycloparaffins has a boiling point of 140-170° C.

* * * * *